United States Patent [19]

Toki et al.

[11] Patent Number: 4,621,228

[45] Date of Patent: Nov. 4, 1986

[54] ELECTRIC MOISTURE METER

[75] Inventors: Kuni Toki, Kawasaki; Osamu Sindou, Tokyo, both of Japan

[73] Assignee: Kett Electric Laboratory, Tokyo, Japan

[21] Appl. No.: 669,973

[22] Filed: Nov. 9, 1984

[30] Foreign Application Priority Data

May 21, 1984 [JP] Japan .................. 59-102430

[51] Int. Cl.[4] ............ G01R 27/02; G01R 15/10; G01R 27/26

[52] U.S. Cl. ................ 324/61 R; 364/571

[58] Field of Search ....... 364/550, 571, 506, 507; 73/73; 324/65 R, 61 R, 61 P

[56] References Cited

U.S. PATENT DOCUMENTS

| | | | |
|---|---|---|---|
| 4,150,433 | 4/1979 | Kaniel | 364/571 |
| 4,193,116 | 3/1980 | Funk . | |
| 4,303,984 | 12/1981 | Houvig | 364/571 |
| 4,390,956 | 6/1983 | Cornforth | 364/571 |
| 4,399,404 | 8/1983 | Resh | 324/61 R |
| 4,408,128 | 10/1983 | Fujita | 324/65 R |
| 4,513,616 | 4/1985 | Bezard | 364/571 |

FOREIGN PATENT DOCUMENTS

| | | | |
|---|---|---|---|
| 3128095 | 2/1983 | Fed. Rep. of Germany | 364/571 |
| 56-70453 | 11/1979 | Japan . | |
| 0982007 | 12/1982 | U.S.S.R. | 364/573 |
| 1017993 | 5/1983 | U.S.S.R. . | |

OTHER PUBLICATIONS

Kulikovsky: "Radio and Electronics Handbook"–Energia–Moskow, 1970 (in Russian)–Chapter 24.

Primary Examiner—Reinhard J. Eisenzopf
Assistant Examiner—Jose M. Solis
Attorney, Agent, or Firm—Pollock, Vande Sande & Priddy

[57] ABSTRACT

A voltage signal associated with the moisture content of a sample in grain or sand form is converted into a digital signal value by an analog-to-digital converter. A programmable read-only memory capable of erasure and field rewriting has stored therein conditions for computation and calibration parameters associated with various types of the sample. Upon designation of one of the types, the conditions for computation for the designated type of sample are picked up, and a moisture content is computed and digitally indicated by use of the computation parameters for the designated sample type. This moisture content value can be compensated for temperature, and the conditions for computation and the calibration parameters in EPROM are capable of being erased or rewritten.

3 Claims, 7 Drawing Figures

ELECTRIC MOISTURE METER

BACKGROUND OF THE INVENTION

1. Field of the Invention

The present invention relates to an electric moisture meter, in particular to an electric moisture meter for measuring and indicating the water content of a sample.

If the quality of a cereal product is to be maintained and the shelf life following the reaping thereof is to be lengthened, the water content thereof is required to be regulated properly. When the moisture content of the cereal product is too low, the taste thereof as a food is deteriorated greatly even though the shelf life thereof may be long, while if the moisture content is too high, on the other hand, bacteria will multiply to cause decomposition thereof.

In calculation of the yield of a cereal product, the moisture content of a small amount of sample thereof is measured to correct the yield. In the case where the moisture content of a 100 g sample collected from a ton of cereal product, for instance, an error of moisture content measurement of 1% by weight will cause an yield error of 10 kg ($=1$ ton$\times 1\%$).

The forecasting of the yield of cereal products important to our dietary life is essential for enabling us to take action against an unbalanced demand and supply of particular cereal product. Such a forecasting of course greatly depends on the weather and rainfall of the year involved. The accumulated effect of the weather conditions of the year presents itself on the yield of the cereals several months before the reaping thereof, and the moisture content of the sample collected at that time is measured in the same manner as mentioned above. The resultant measurement data will be useful to secure a balanced demand and supply of the cereals in the market thereof.

2. Description of the Prior Art

An electric moisture meter is disclosed in U.S. Pat. No. 4,408,128 dated Oct. 4, 1983, granted to Fujita and assigned to the same assignee as the present assignee. An electric moisture meter is a device operating on the principle that the electric capacity of a sample held between positive and negative electrodes is measured, and the value of moisture content thereof is indicated on the basis of the correlation studied in advance between the moisture content and the electrical characteristics. This correlation varies with the type and quality of a cereal product involved on the one hand and with the country or area of production on the other hand. Due to the variations in grain size, for example, a single moisture meter fails to serve the purpose of all cereal products. There are probably four to five types of cereal products of which the moisture content is to be measured in a single area. It is, therefore, necessary to provide a moisture meter having correlations calibrated for five respective cereal products according to the type or grain size. In order for a moisture meter to be used for an area different from the area where the meter has so far been used, on the other hand, the correlationship contained in the particular meter is required to be changed. Further, the apparent difference in the water content value caused by the differences of temperature at the time of measurement makes correction by temperature desirable.

SUMMARY OF THE INVENTION

Accordingly, it is an object of the present invention to provide an electric moisture meter containing several variable correlationships between the moisture content and electric characteristics of several types of cereal products, and thus indicating the water content of the respective cereal products.

Another object of the present invention is to provide an electric moisture meter which stores variable correlationships between moisture content and electrical characteristics in multiple combinations of cereal products and which directly indicates the temperature-compensated water content of the respective cereal products.

According to the present invention, there is provided an electric moisture meter comprising a plurality of keys for designating the type of a cereal product sample filled between the electrodes of the meter, a moisture content measuring circuit for producing a voltage signal representing the moisture content of the sample, an analog-to-digital converter for producing a digital signal value corresponding to the voltage signal, a programmable read-only memory (EPROM) capable of being erased and rewritten for storing the parameters for calculations according to the type of cereal, a processing unit for producing a moisture content value calculated from the calculation parameters read out cf EPROM in response to the digital signal value and the signal representing the type of cereal product, and a display unit for digitally displaying the moisture content.

DESCRIPTION OF THE PREFERRED EMBODIMENTS

Figure 1:
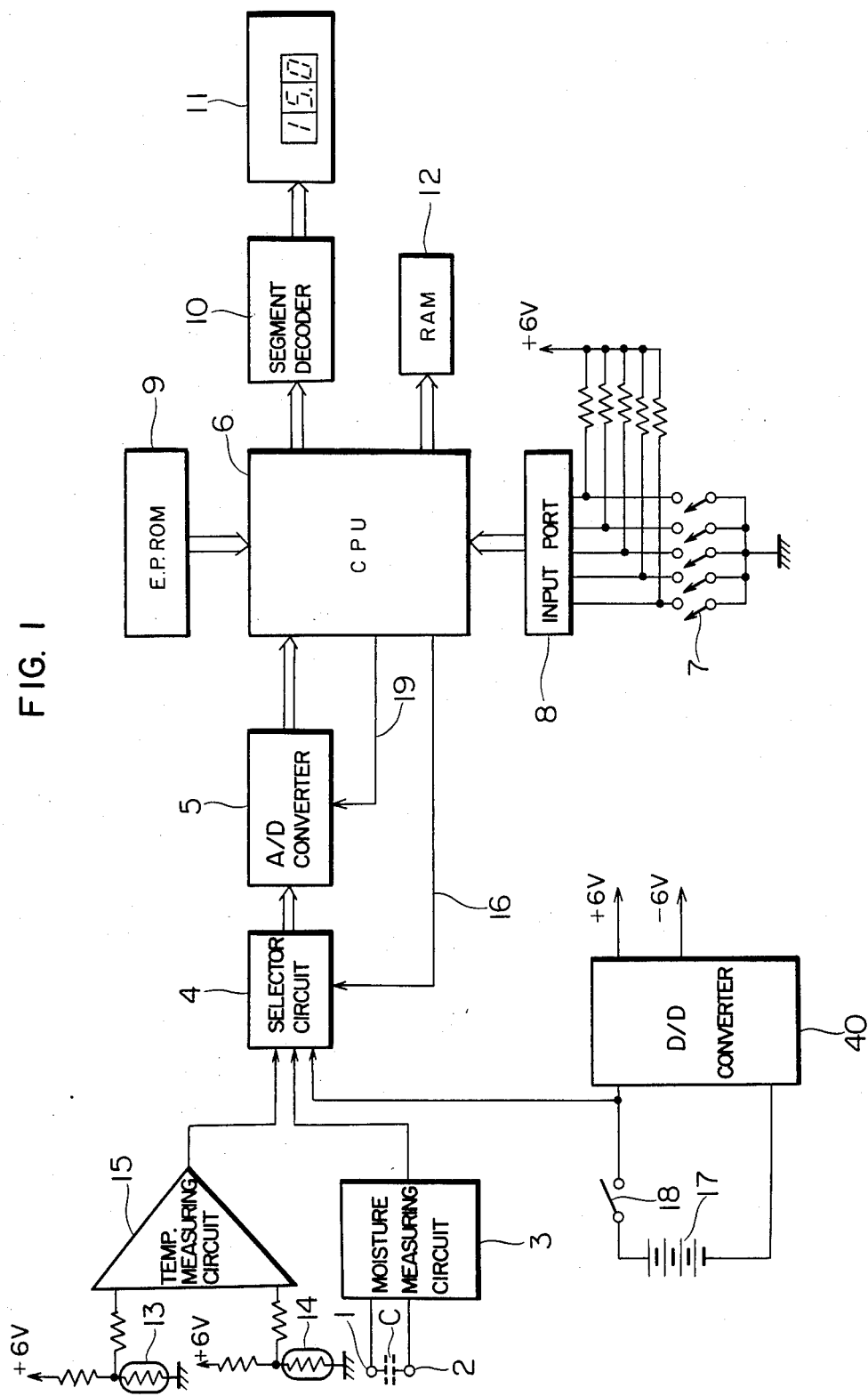
FIG. 1 is a block diagram showing a moisture meter according to the present invention.

A block diagram of the circuit of a moisture meter according to the present invention is shown in FIG. 1.

Figure 5:
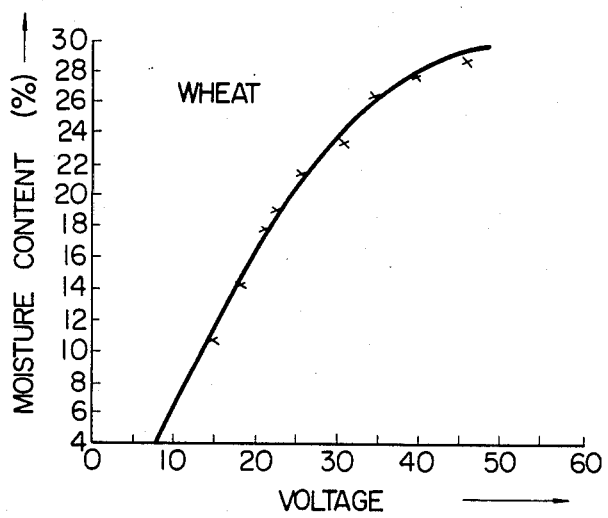

The electric capacity between a couple of electrodes 1 and 2 arranged in a case containing a cereal product sample is increased by the dielectric constant of the cereal product, or especially, the dielectric constant of the water contained in the cereal product. This change of capacity C is produced at a moisture content measuring circuit 3 as a DC voltage signal of 180 mV, for instance, and through an input-switchable selector circuit 4 subject to control by a control line 16, is applied to an A/D converter 5. The signal converted into a digital value such as D=18.0 is then applied to a CPU 6. The operation of A/D converter 5 is controlled by CPU 6 through a control line 19. The type of the cereal product contained in the case is designated by selection of one of five keys 7. The type of the cereal product, say, wheat, is supplied to the microprocessor 6 through an input port 8. The microprocessor 6 reads from the EPROM 9, which can electrically store or erase the memory thereof, the assumed moisture (or tentative moisture) content calculation parameters shown below representing the relation between voltage and moisture content as illustrated in FIG. 5.

A = −0.01361
B = 1.39707
C = −6.06255 where A, B and C designate constant terms of the second, first and zeroth degrees respectively of a quadratic equation. A calculation for determining the assumed moisture value M is carried out by use of RAM 12.

$$M = AD^2 + BD + C \qquad (1)$$

If a CPU containing a RAM is used, this external RAM 12 is not required.

The sum of a couple of voltage signals supplied from a couple of platinum resistance thermometer elements 13 and 14 arranged at two distant points on the specimen represent average temperature signals. These signals are amplified by a temperature measuring circuit 15, and through the selector circuit 4, are applied to the A/D converter 5, where the signals are converted into digital temperature values as in the case of moisture content data, the resulting signal being applied to the CPU 6.

The variations of moisture content with the temperature measurements depend on the type of the cereal product, and the temperature-compensating parameters for the five types of cereal products are stored in the EPROM 9. Since wheat is already specified as the type of cereal product, the temperature coefficient calculation parameters for wheat, that is, a = 0.00139
b = −0.0244
c = 0.15067 are read out of the EPROM 9 by the CPU 6. The assumed moisture content value M already calculated is compensated by use of these parameters, as follows:

$$F = aM^2 + bM + c \qquad (2)$$

The temperature compensation L is based on the measuring temperature of 30° C. and is used for correcting the digital value D $$L = (T - 30)F \qquad (3)$$

$$X = D - L \qquad (4)$$

A target moisture content value Y is determined from the equation below by use of the assumed moisture content calculation parameters mentioned above.

$$Y = AX^2 + BX + C \qquad (5)$$

The value Y depends on the assumed moisture content M. About three times of the arithmetic operations of the equations (1) to (5) to the value Y are repeated to refine the value Y, so that it is near the true moisture content. (If the measured temperature is 30° C., the value Y is equal to the assumed moisture content value M of equation (1).) The target moisture content Y = 14.7 of wheat associated with the digital value D = 18.0 is thus obtained.

The figure of this target moisture content is decoded by a 7-segment decoder 10 and indicated on a moisture content indicator 11.

Figure 3:
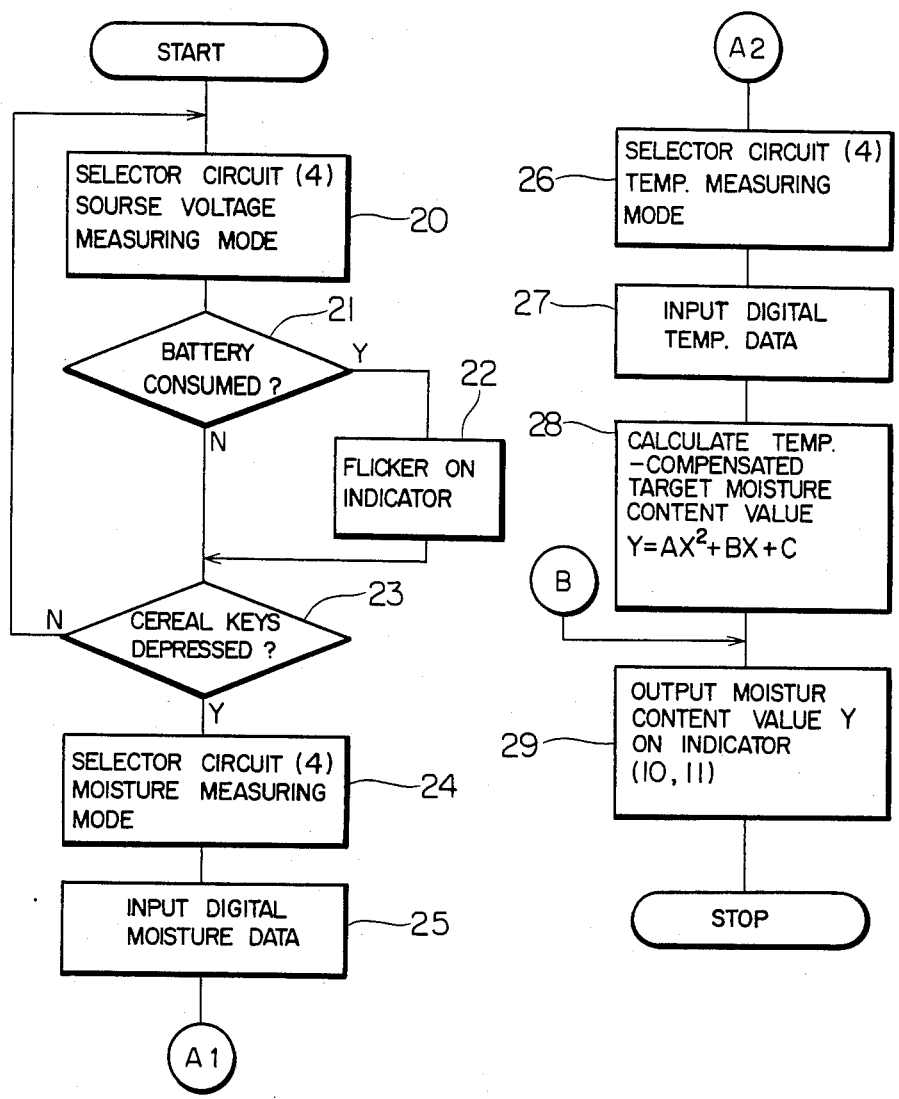
FIG. 3 is a flowchart showing the operation of a moisture meter according to the present invention.

FIG. 3 is a flowchart showing the operation of a moisture meter according to the embodiment described above. The moisture meter according to the embodiment under consideration is actuated by a power supply ±6 V including 174 dry cells of Unit-3 (IEC:AA) of DC 6 volts as DC-DC converted by a D/D converter 40. The CPU 6, EPROM 9, A/D converter 5, selector circuit 4, RAM 12 and the segment decoder 10 employ well-known CMOS circuit elements of small power consumption to lengthen the service life of the battery. This long service life permits the moisture meter to be brought easily into storages of five types of cereal products without any AC power supply for the purpose of moisture content measurement. As the battery begins to be consumed, the moisture meter detects a reduction in the source voltage. The loop of the blocks 20 to 21 to 23 to 20 in the flowchart of FIG. 3 represents a program for detection of the voltage drop. When the voltage drops to a level lower than 4.4 V. the process is passed from the decision block 21 to the flicker indication block 22, so that the flicker continues during the subsequent measurement indication to demand replacement of the battery. The programs for performing such operations as measurement, calculation and indication shown in the flowchart of FIG. 3 are stored, together with the measurement parameters, in the EPROM 9, and start to operate with the turning on of the switch 18.

Figure 2:
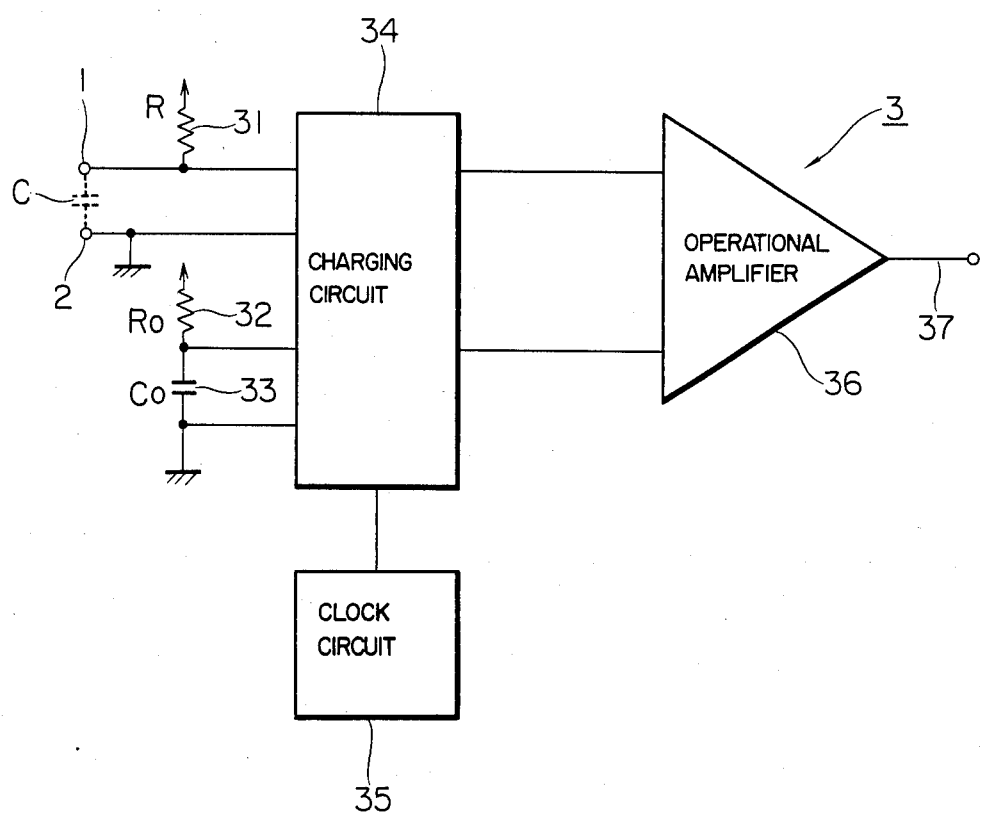
FIG. 2 is a block diagram showing a part of the circuit of a moisture meter according to the present invention.

An example of the moisture content measuring circuit of FIG. 1 will be explained with reference to FIG. 2. A couple of constant-voltage charging circuits C–R and C₀–R₀ are connected to a charging circuit 34, and respectively charged from 0 V to a certain voltage level during a cycle of the output clocks of a clock circuit 35. The resulting voltages are applied to a voltage operational amplifier 36, so that an output voltage proportional to the difference between the two voltages is produced on a line 37 and is applied to the selector circuit in FIG. 1. On the basis of the voltages at the junction points C₀ 33 and R₀ 32, therefore, the voltages at the junction points Ċ and R 31 are obtained. In such a manner that this voltage is significantly lower than the source voltage for charging, the clock period and the constants of the resistors and capacitors are determined.

As a result, the magnitude of moisture content of the cereal product is produced as a magnitude of the output of the operational amplifier 36.

The temperature coefficient calculation parameters or the assumed moisture content calculation parameters representing the relation between moisture content and voltage shown in FIG. 5 are determined in the manner described below. In Japan, the moisture content of a cereal product is determined by a predetermined method. According to a standard method of measurement under the Execution Rules of Agricultural Products Inspection Law, it is stipulated that after a cereal product is kept in an environment of one atmospheric pressure and 105° C., for 5 hours the weight lost is considered as the moisture content of the particular cereal product.

Figure 6:
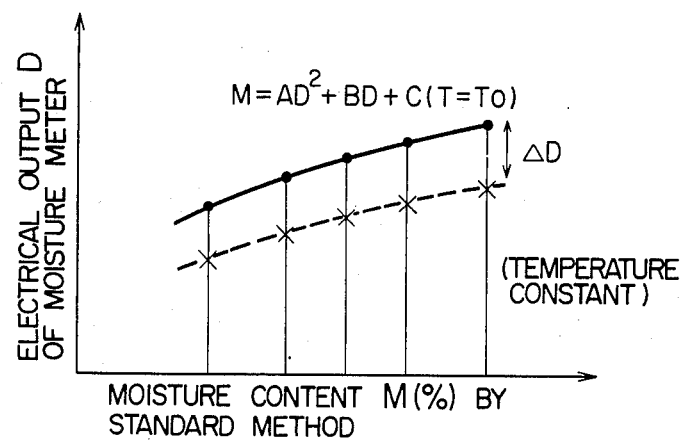
FIGS. 6 and 7 are diagrams for explaining the operating principle and the output variations of a moisture meter according to the present invention.
Figure 7:
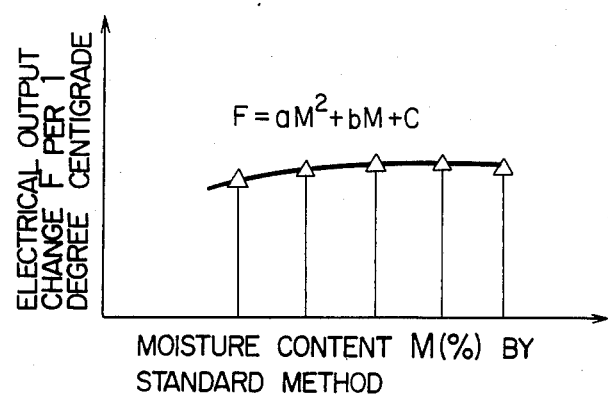

Samples of cereal products having high and low moisture contents are loaded in the moisture meter according to the present invention, and predetermined two keys of the cereal-designating switch 8 are depressed. In the process, the program jumps from the connector A1 to B in FIG. 3, thus producing data before compensation. With the measurement voltage D as cordinate and the moisture content M obtained by the above-mentioned standard measuring method as abscissa, mutually corresponding points are plotted as shown by the solid line in FIG. 6. With the measurement temperature T reduced and maintained at $T_1$, similar measurements are made to obtain the characteristic of the dashed line. The difference D of the measured electric outputs is divided by $T_0-T_1$, and then the electric output change F per degree centigrade is obtained. This change F is measured for several moisture contents M, and the characteristic shown in FIG. 7 is obtained. From the characteristics shown in FIGS. 6 and 7, the parameters A, B, C, a, b, c indicating the characteristics change are determined by regression and stored in EPROM. The straight line in FIG. 4 and the quadratic curve in FIG. 5 are characteristics curves based on the parameters thus determined.

Figure 4:
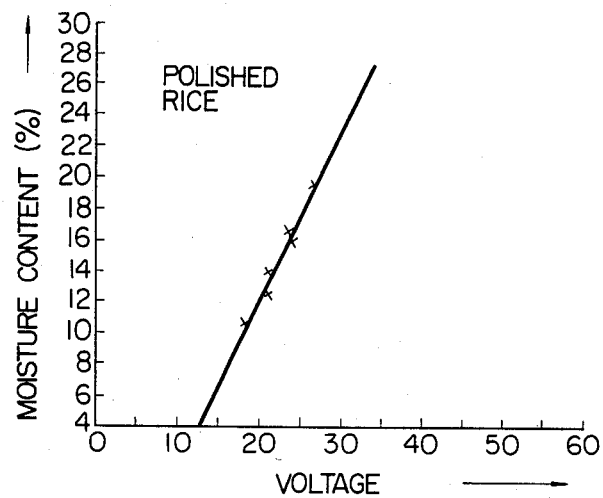
FIGS. 4 and 5 show characteristics representing the relation between the moisture content of a cereal product and the voltage measured therefrom.

In many cereal products, the changes of both the characteristics of the electric output D and the electrical output change F per degree centigrade are capable of being expressed by a linear equation. FIG. 4 is a diagram showing the moisture content in % of polished rice based on the standard method as against the electrical output D. FIG. 5 shows the wheat characteristic which cannot be expressed by a linear equation. It is a rare cereal product that has a complex curve requiring a cubical equation.

The parameters of the five types of cereal products stored in the EPROM of the moisture meter under consideration may be erased by an electrical method or by radiation of ultraviolet ray after removing the EPROM 9 from the IC socket on the circuit board of the apparatus, after which the EPROM 9 may be mounted on the EPROM writer to change the contents of memory.

The object of measurement, which is made up of a cereal product in the foregoing description of embodiments, is not limited to cereal products but any solid in grain or sand form.

We claim:

1. An electrical moisture meter for indicating the moisture content of a cereal sample filled between two electrodes thereof comprising:
    (a) a plurality of keys for designating the type of the sample;
    (b) a moisture content measuring circuit for producing a voltage signal representing said moisture content;
    (c) a temperature measuring circuit including a temperature sensor arranged near said sample for producing a measured temperature signal;
    (d) an analog to digital converter circuit for producing a digital signal value corresponding to an input analog voltage signal;
    (e) a selector circuit connected to both of said moisture content and temperature measuring circuits for receiving said measured temperature signal and said moisture content signal, and applying one of said signals to said analog to digital converter;
    (f) a programmable read only memory EPROM capable of erasure and rewriting for storing parameters for computation according to the type designated, said EPROM storing temperature computation parameters for each type of sample, said EPROM mounted on an IC socket for easy replacement, and said EPROM written with said computation parameters determined on the basis of original data measured from said moisture content measuring circuit;
    (g) a processor unit for producing a moisture content value calculated on the basis of the computation parameters read from said EPROM in accordance with the type designated by said plurality of keys, said processor determining a moisture content value based upon a digital signal received from said analog to digital converter circuit representing the measured moisture content and temperature of said sample, said processor applying either a resulting calculated temperature compensated moisture content value to an indicator, or measured original moisture data at the selection of said keys, said processor further calculating said computation parameters based upon original data, and writing said computation parameters in said EPROM, whereby subsequent measured moisture data may be modified on the basis of said stored computation parameters to derive said temperature compensated moisture content value; and
    (h) an indicator for indicating said temperature compensated moisture content value in digital form.

2. An electric moisture meter according to claim 1, said moisture content circuit including:
    a couple of constant-voltage charging circuits;
    a charging circuit connected with said coupled of constant-voltage charging circuits, one of said constant-voltage charging circuits including said two electrodes;
    a clock circuit for providing a period of charging said couple of constant-voltage charging circuit; and
    an operational amplifier for providing a voltage difference between the two outputs of said couple of constant-voltage charging circuits.

3. A method for electrically measuring and indicating the moisture content of a sample of a cereal filled between two electrodes thereof, comprising:
    producing a digital signal representing the moisture content of said sample;
    measuring the temperature near said sample and producing a digital signal representative thereof;
    reading computation parameters from a removable programmable memory EPROM;
    processing said digital signals in a processor to determine said computation parameters for each type of cereal encountered, and writing said computation parameters into said programmable memory;
    calculating subsequent moisture levels based on said stored computation parameters and subsequent values of said digital signals; and
    displaying during writing of said programmable memory, said moisture content digital signals, and said subsequent values of digital signals.

* * * * *